United States Patent [19]

Miyanaga et al.

[11] Patent Number: 4,500,431
[45] Date of Patent: Feb. 19, 1985

[54] SEPARATION OF ANALYSIS OF ANIONS

[75] Inventors: Akiyoshi Miyanaga; Yukitada Kurihara, both of Yokohama, Japan

[73] Assignee: Toyo Soda Manufacturing Co. Ltd., Yamaguchi, Japan

[21] Appl. No.: 548,828

[22] Filed: Nov. 4, 1983

[30] Foreign Application Priority Data

Nov. 9, 1982 [JP] Japan ............................. 57-195236

[51] Int. Cl.$^3$ ............................................. B01D 15/08
[52] U.S. Cl. ..................................... 210/656; 210/198.2
[58] Field of Search ....................... 210/656, 659, 198.2

[56] References Cited

PUBLICATIONS

"Sodium and Potassium Benzoate and Benzoic Acid as Eluents for Ion Chromatography," D. T. Gjerde and J. S. Fritz, Anal. Chem., vol. 53, No. 14, pp. 2324–2327, (Dec. 1981).

"Single–Column Ion Chromatography for the Determination of Chloride and Sulfate in Steam Condensate and Boiler Feed Water," K. M. Roberts, D. T. Gjerde and J. S. Fritz, Anal. Chem., vol. 53, No. 11, pp. 1691–1695, (Dec. 1981).

"Factors Affecting the Resolution and Detectability of Inorganic Anions by Non-Suppressed Ion Chromatography," J. A. Glatz and J. E. Girard, J. of Chromatographic Sciences, vol. 20, pp. 266–273, (Jun. 1982).

Introduction to Modern Liquid Chromatography by Snyder et al., John Wiley & Sons of New York, p. 425, (1979).

Fundamentals of Chromatography by Cassidy, Interscience Publishers of New York, pp. 312–314, (1957).

*Primary Examiner*—John Adee
*Attorney, Agent, or Firm*—Sherman & Shalloway

[57] ABSTRACT

This invention makes a rapid and accurate anion separation analysis possible by using an electric conductivity detector built in a chromatographic apparatus and a binary composite solution as an eluent. The binary composite solution: borax and an aliphatic acid/an aromatic acid/a saccharic acid/a sugar is used in alkaline regions, while the binary composite solution: a sulphonic acid and boric acid/a monocarboxylic acid is used in acid regions. Over a conventional analysis employing phthalic acid or benzoic acid singly, this analysis has an advantage in capturing a wider variety of anions on chromatograph with high accuracy in more sensitized condition without suffering a hindrance due to noises or peaks having nothing to do with objective anions because the electric conductivity of the eluent itself is very low.

16 Claims, 10 Drawing Figures

SEPARATION OF ANALYSIS OF ANIONS

FIELD OF THE INVENTION

This invention relates to a separation analysis of anions by the use of an electric conductivity detector coupled with liquid chromatography. Thus, this invention is characterized particularly by being able to analyse objective anions with high accuracy in a very short time by changing the composition, concentration and pH of an eluent to be used.

DESRIPTION OF THE PRIOR ART

The liquid chromatography combined with an electric conductivity detector was first developed by H Small, T. S. Stevens and W. C. Bauman (Anal. Chem., 47, 1801 (1975)); it has been employed since then as the ion chromatography. However, since the chromatography requires a special cation exchange column or a special cation exchange membrane tube in order to change a carbonate into carbonic acid, the chromatography needs a pump that can circulate a special solution at a constant rate to refresh the column or tube mentioned above. As a result, the structure of the device inevitably becomes complex.

Other than that, G. T. Gjerde, J. S. Fritz and others (J. Chromatogr. 176, 199 (1979)) have tried to analyse anions by using only a separation column packed with an anion exchange resin. But it has become evident that crucial troubles arise when limited organic acid such as phthalic acid or benzoic acid is used singly as an eluent in the analysis.

Namely, a peak assignable to that special organic acid appears on the chromatogram, and this hinders the detection of objective anions in the separation analysis. To make matters worse, especially in acid regions, it takes a lot of time until the peak disappears by elution, so that it is practically impossible to carry out many cycles of analysis successively in a short limited time. Moreover, in regard to anions like phosphate ion, which varies its ionization valence according to the pH of an eluent, using phthalic acid or benzoic acid singly as a buffer has essentially a limit in controlling pH. Practically, if phosphate ion is present together with fluoride ion, chloride ion, bromide ion, nitrite ion, nitrate ion and sulphate ion in the same system, it is very difficult to determine these ions quantitatively by the use of an electric conductivity detector within a short time.

SUMMARY OF THE INVENTION

Under the circumstances, the present inventors have established a speedy, accurate, all-purpose and cheap separation analysis of anions by eliminating troubles arising when inorganic anions are separated by the single use of conventional columns and by studying various conditions related to eluent; thus, they have finally accomplished this invention.

That is, the present invention is a separation analysis through liquid chromatography, which is characterized in that a solution prepared by mixing two components A and B is used as an eluent, where the component A is at least one compound selected from the group consisting of an aliphatic polycarboxylic acid, an aliphatic hydroxycarboxylic acid, an aromatic organic acid, a saccharic acid, a sugar and a sulphonate and the component B is at least one compound selected from the group consisting of borax, boric acid and an aliphatic monocarboxylic acid.

Figure 1:
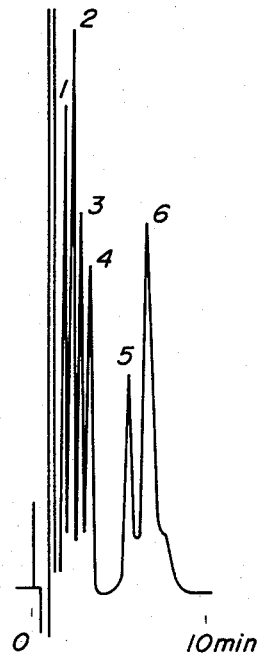
FIG. 1 is a chromatogram illustrating the result of a separation analysis of anions by the use of an eluent prepared by mixing an aliphtic organic acid and borax.

In these figures, the numeral 1 shows chloride ion, the numeral 2 shows nitrite ion, the numeral 3 shows bromide ion, the numeral 4 shows nitrate ion, the numeral 5 shows phosphate ion, the numeral 6 shows sulphate ion, the numeral 7 shows fluoride ion, the numeral 8 shows carbonate ion, the numeral 9 shows acetic acid and the numeral 10 shows formic acid.

DETAILED DESCRIPTION

The composition of a device for the present separation analysis does not differ at all from the composition of conventional devices employed for usual liquid chromatography. Briefly, the device for this separation analysis is composed of a solution circulating pump, an anion exchange column and an electric conductivity detector.

As a result of extensive study, the present inventors have succeeded in capturing a considerably wider variety of anions rapidly in highly sensitized condition, compared with conventional methods, by using a solution which contains a compound of the component A and a compound of the component B instead of using phthalic acid or benzoic acid singly.

Among many possible combinations, such combination series as an aliphatic polycarboxylic acid plus borax, an aliphatic hydroxycarboxylic acid plus borax, an aromatic organic acid plus borax, a saccharic acid plus borax and a sugar plus borax or such combination series as a sulphonate plus boric acid and a sulphonate plus an aliphatic monocarboxylic acid are especially desirable. In this context, the aliphatic polycarboxylic acid means an aliphatic dicarboxylic acid, an aliphatic tricarboxylic acid, etc.; the aliphatic hydroxycarboxylic acid means a monohydroxydicarboxylic acid, a dihydroxydicarboxylic acid, a monohydroxytricarboxylic acid, etc.; and the aromatic organic acid means an aromatic monocarboxylic acid, an aromatic dicarboxylic acid, an aromatic tricarboxylic acid, an aromatic hydroxycarboxylic acid and an aromatic sulphocarboxylic acid. Hereinafter the aliphatic polycarboxylic acid and the aliphatic hydroxycarboxylic acid are collectively referred to as an aliphatic organic acid.

Concretely, the following compounds are practically available for this separation analysis. That is, the aliphatic organic acid mentioned above comprises citric acid, adipic acid, tartaric acid, malic acid and glutaric acid. The aromatic organic acid mentioned above comprises phthalic acid, benzoic acid, sulphosalicylic acid, sulphobenzoic acid and trimesic acid. The saccharic acid mentioned above comprises glucuronic acid, gluconic acid and galactonic acid. The sugar mentioned above comprises glucose, lactose and fructose. The sulphonic acid mentioned above comprises hexanesulphonic acid, octanesulphonic acid, decanesulphonic acid, benzenesulphonic acid, benzenedisulphonic acid, naphthalenesulphonic acid and naphthalenedisulphonic acid. The monocarboxyiic acid mentioned above comprises formic acid, acetic acid and propionic acid.

Meantime, in this invention it is important to note that when chloride ion, nitrite ion, bromide ion, nitrate ion, sulphate ion and phosphate ion are in need of determination by the use of an eluent composed of the organic acid and borax or the sugar and borax, the concentration of the organic acid, the sugar and borax has to be in the range $1 \times 10^{-4} - 5 \times 10^{-3}$ mole respectively on condition that the pH of the composite eluent is adjusted in the range 7.5–11.0, or preferably adjusted in the range 8.5–9.5 with potassium hydroxide or boric acid. Again, in this invention it is also important to note that when anions are in need of determination by the use of an eluent composed of the sulphonic acid and boric acid or the sulphonic acid and the monocarboxylic acid, the concentration of the sulphonic acid has to be in the range $1 \times 10^{-4} - 5 \times 10^{-3}$ mole and the concentration of boric acid monocarboxylic acid has to be in the range $1 \times 10^{-2} - 1 \times 10^{-1}$ mole on condition that the pH of the composite eluent is adjusted in the range 3.0–6.0, preferably adjusted in the range 4.5–5.5 with sodium hydroxide or potassium hydroxide. In regard to the latter process, it is equally possible to add boric acid or the monocarboxylic acid to a sodium sulphonate or potassium sulphonate solution directly whose concentration is in the range $1 \times 10^{-4} - 5 \times 10^{-3}$ mole in order that the pH of the composite eluent may be settled in the range 4.5–5.5.

As seen from the above, this invention has made it possible to detect a number of anions very fast by means of the composite eluent and an electric conductivity detector coupled with the anion exchange chromatography. In this separation analysis, as long as a solution composed of the aliphatic organic acid and borax, the aromatic organic acid and borax, saccharic acid and borax or the sugar and borax is used as an eluent, peaks of all kinds of ions appear on the positive side of chromatogram as shown in Examples 1, 2, 3 and 4. However, when phthalic acid is used singly as an eluent in a conventional manner, the peak assignable to phosphate ion appears on the negative side of chromatogram as shown in the Comparative Examples 1 and 2. For this reason this has long been a hindrance to the quantitative analysis of phosphate ion.

In contrast to this, it is surprising enough that this invention first made possible a rapid quantitative analysis of not only phophate ion but also various kinds of anions by means of a special eluent.

What is more, in acid regions phthalic acid or benzoic acid has been used as an eluent in order to detect anions accurately. However, with this the electric conductivity of the eluent itself being as high as 400–600 $\mu$S, noises on the base line are accordingly so high as shown in Comparative Example 3 that in the analysis of chloride ion the detectable lowest concentration limit (S/N>3) has been considered 30 ppb. More than that, there appear many high peaks having no relation with objective ions on the negative side of chromatogram and they have been an obstacle to the detection. In comparison with this, when an eluent composed of the sulphonic acid and boric acid or composed of the sulphonic acid and the monocarboxylic acid is used in the separation analysis, the capacity of detecting inorganic anions is improved very much because the electric conductivity of the eluent itself is lowered to below 200 $\mu$S as shown in Examples 5 and 6. In consequence, the detectable lowest concentration limit for chloride ion (S/N>3) is lowered to 5 ppb. Again, since any peak does not appear on the negative side of chromatogram, a rapid and successive determination of anions can be conducted successfully.

This invention will be described in more detail according to the following examples and comparative examples.

EXAMPLE 1

A stainless steel column of the length 5 cm and the inner diameter 4.6 mm, packed with an anion exchanger (a product of Toyo Soda Manufacturing Co., Ltd., Type: TSK GEL IC-620 SA) whose particle size is 10 $\mu$m and whose ion exchange capacity is 0.03 milliequivalent a gram, was mounted on a liquid chromatographic apparatus (a product of Toyo Soda Manufacturing Co., Ltd., Type: HLC-601) especially designed for this invention.

With an electric conductivity detector built in the chromatographic apparatus, an authentic inorganic anion mixture which contained 4 ppm of chloride ion, 8 ppm of nitrite ion, 8 ppm of bromide ion, 8 ppm of nitrate ion, 12 ppm of phosphate ion, and 8 ppm of sulphate ion was subjected to the separation analysis at the measurement range of 4 $\mu$SFS at the flow rate 1.2 ml/min.

In this separation analysis, a solution which contained 0.5 millimole of adipic acid and 1.0 millimole of borax was used as an eluent after the pH of the solution was adjusted to 9.0 with KOH.

FIG. 1 shows a chromatogram obtained from 100 $\mu$l of the authentic inorganic anion mixture. As best seen from this, all peaks attributable to all ions (including phosphate ion) appeared on the positive side of the chromatogram.

EXAMPLE 2

Figure 2:
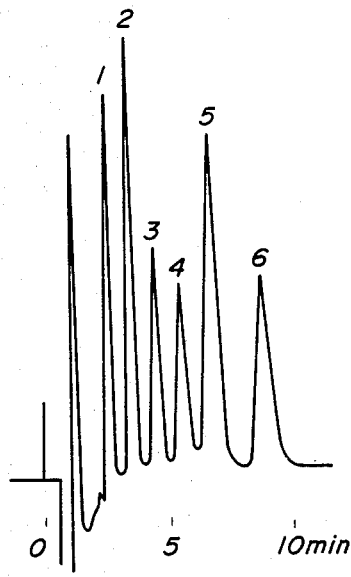
FIG. 2 is a chromatogram illustrating the result of a separation analysis of anions by the use of an eluent prepared by mixing an aromatic organic acid and borax.

A series of operations was carried out in the same way as in Example 1, except that an eluent was prepared by mixing 0.5 millimole of m-sulphobenzoic acid and 1.0 millimole of borax and that the pH of the eluent was adjusted to 9.7 with potassium hydroxide. The result of the separation analysis is shown in FIG. 2.

EXAMPLE 3

An eluent was prepared by mixing 1.3 millimoles of potassium gluconate and 1.3 millimoles of borax. The pH of the eluent was adjusted to 8.5 with boric acid. After that, in order to prompt full separation of ions in the solution, 12% of acetonitrile and 0.3% of glycerin were added respectively based on the weight of the solution.

Figure 3:
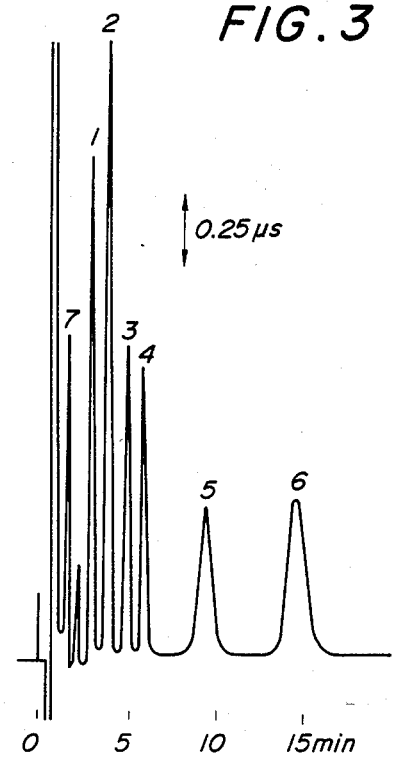
FIG. 3 is a chromatogram illustrating the result of a separation analysis of anions by the use of an eluent prepared by mixing a saccharic acid and borax.

An anion mixture containing 1.0 ppm of fluoride ion, 2.0 ppm of carbonate ion, 2.0 ppm of chloride ion, 4.0 ppm of nitrite ion, 4.0 ppm of bromide ion, 4.0 ppm of nitrate ion, 6.0 ppm of phosphate ion and 4.0 ppm of sulphate ion was subjected to the separation analysis at the measurement range of 2.5 $\mu$SFS. FIG. 3 shows the resulting chromatogram.

EXAMPLE 4

Figure 4:
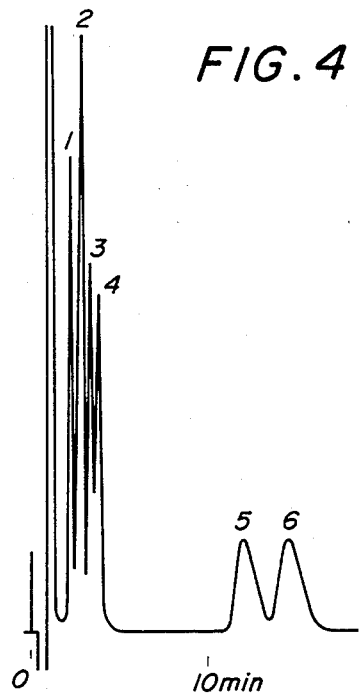
FIG. 4 is a chromatogram illustrating the result of a separation analysis of anions by the use of an eluent prepared by mixing a sugar and borax.

A series of operations was conducted in the same way as in Example 1, except that an eluent was prepared by mixing 1.0 millimole of glucose and 1.0 millimole of borax and that the pH of the eluent was adjusted to 9.2 with KOH. FIG. 4 shows the result of the determination of the anion mixture.

COMPARATIVE EXAMPLE 1

Figure 5:
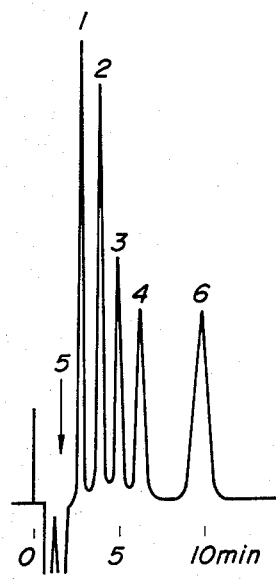
FIG. 5 is a chromatogram illustrating the result of a separation analysis of anions by the use of an eluent prepared by adjusting the pH of phthalic acid to 6.5.

An eluent was prepared by adjusting the pH of a 1 millimole potassium hydrogenphthalate solution to 6.5 with KOH. Except that, every operation was conducted in the same way as in Example 1. FIG. 5 shows the result of the determination of the anion mixture. Compared with Examples 1, 2, 3 and 4, it was proved that peaks assignable to chloride ion, nitrite ion, bromide ion, nitrate ion and sulphate ion appeared on the positive side of chromatogram and the retention time of each ion did not change so significantly. Despite that, because a peak due to phosphate ion appeared on the negative side of chromatogram and its retention time shortened, it was impossible to carry out a quantitative analysis.

COMPARATIVE EXAMPLE 2

Figure 6:
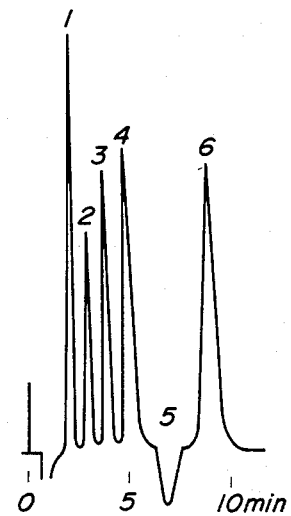
FIG. 6 is a chromatogram illustrating the result of a separation analysis of anions by the use of an eluent prepared by adjusting the pH of phthalic acid to 9.0.

After its pH having been adjusted to 9.0 with KOH, a 1 millimole potassium hydrogenphthalate solution was used as an eluent. Except that, all operations were carried out in the same way as in Example 1. FIG. 6 shows the determination result of the anion mixture.

Compared with Comparative Example 1, it has become clear that the retention time of phosphate ion is also present between both the retention time of nitrate ion and sulphate ion as seen in Examples 1, 2, 3 and 4. Nevertheless, since a peak attributable to phosphate ion appeared on the negative side of chromatogram, to make a quantitative analysis was impossible.

EXAMPLE 5

Figure 7:
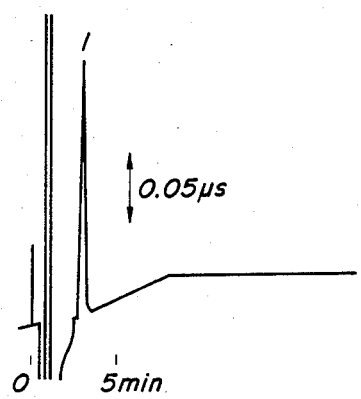
FIG. 7 is a chromatogram illustrating the result of a highly sensitized chloride ion detection by the use of an eluent prepared by mixing a sulphonic acid and boric acid.

Except that a solution containing 2 millimoles of sodium n-octanesulphate and 7.0 millimoles of boric acid was used as an eluent and that determination was conducted at the measurement range of 0.5 $\mu$SFS, all operations were made in the same way as in Example 1 to determine 100 ppb of chloride ion. The result is shown in FIG. 7.

The electric conductivity of the eluent itself was 195 $\mu$S. Under this condition, 5 ppb was the detectable lowest concentration limit for chloride ion.

EXAMPLE 6

Figure 8:
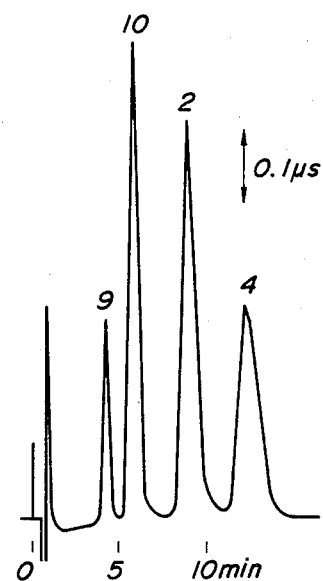
FIG. 8 is a chromatogram illustrating the result of a separation analysis of acetic acid ion, formic acid ion, nitrite ion and nitrate ion by the use of an eluent prepared by mixing a sulphonic acid and boric acid.

A solution, prepared by mixing 0.5 millimole of sodium n-octanesulphonic acid and 5.0 millimoles of boric acid and then adding 5% of acetonitrile, was used as an eluent. Except that the measurement range was set to 1 $\mu$SFS and that the rate of flow in the column was kept 1.3 ml/min., all operations were conducted in the same way as in Example 1. In this example, a solution containing 5.0 ppm of acetic acid, 5.0 ppm of formic acid, 5.0 ppm of nitrous acid and 5.0 ppm of nitric acid was subjected to the separation analysis. The result is given in FIG. 8. The electric conductivity of the eluent itself was 45 $\mu$S.

EXAMPLE 7

Figure 9:
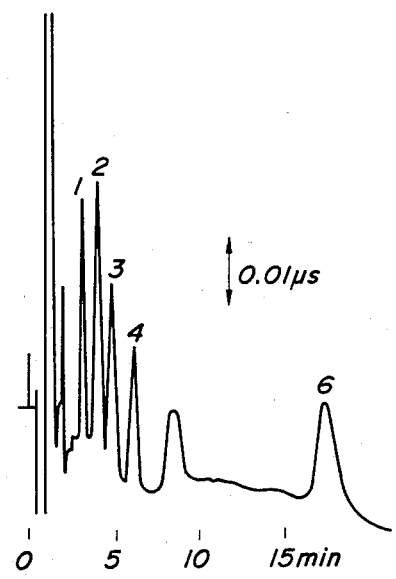
FIG. 9 is a chromatogram illustrating the result of a highly sensitized anion detection by the use of an eluent prepared by mixing a sulphonic acid and a monocarboxylic acid.

With acetic acid used for an amino acid analysis, the pH of a 0.15 millimole sodium m-benzenesulphonate solution was adjusted to 5.0. Except that the measurement range was set to 0.1 $\mu$SFS, all operations were made in the same way as in Example 1. In this example, a solution containing 100 ppb of chloride ion, 200 ppb of nitrite ion, 200 ppb of bromide ion, 200 ppb of nitrate ion and 200 ppb of sulphate ion was subjected to the separation analysis. The result is shown in FIG. 9. The electric conductivity of the eluent itself was 60 $\mu$S. Under this condition, the detectable lowest concentration limit was 5 ppb for chloride ion, 10 ppb for nitrite ion, 20 ppb for bromide ion, 20 ppb for nitrate ion and 30 ppb for sulphate ion.

COMPARATIVE EXAMPLE 3

Figure 10:
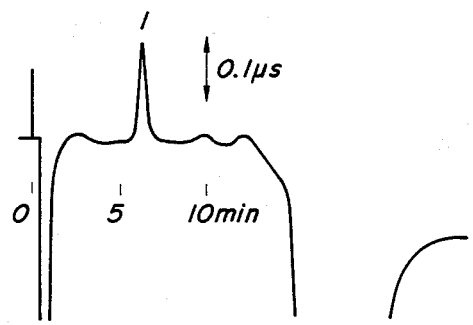
FIG. 10 is a chromatogram illustrating the result of a separation analysis of chloride ion by using benzoic acid as an eluent.

An amount of potassium hydroxide solution was added to a 2 millimole benzoic acid solution so as to settle the pH of the resulting composite solution to 5.5. This composite solution was used as an eluent. Except that the measurement range was set to 1 $\mu$SFS, all operations were made in the same way as in Example 1. The determination result of a solution which contained 100 ppb of chloride ion is shown in FIG. 10.

The electric conductivity of the eluent itself was 450 $\mu$S and this value was so much higher than those of the diluents in Examples 5, 6 and 7 that the detectable lowest concentration limit was raised; thus, the detection sensitivity decreased to 1/5 or less, compared with Examples 5 and 7.

Moreover since a large peak appeared on the negative side of the chromatogram which had never been seen in Examples 5, 6 and 7, a lot of time wasted in determination. On account of that, it was not possible to carry out many cycles of sample analysis successively in a short time.

What we claim is:

1. A separation analysis of anions through liquid chromatography, which is characterized in that a solution prepared by mixing two components A and B is used as an eluent, where the component A is at least one compound selected from the group consisting of an aliphatic polycarboxylic acid, an aliphatic hydroxycarboxylic acid, an aromatic organic acid, a saccharic acid, a sugar and a sulphonate and the component B is at least one compound selected from the group consisting of borax, boric acid and an aliphatic monocarboxylic acid.

2. A separation a of anions as set forth in claim 1, in which Component A is an aliphatic dicarboxylic acid.

3. A separation analysis of anions as set forth in claim 1, in which the Component A is an aliphatic tricarboxylic acid.

4. A separation analysis of anion as set forth in claim 1, in which the Component A is a hydroxydicarboxylic acid.

5. A separation analysis of anions as set forth in claim 1, in which the Component A is a dihydroxydioarboxylic acid.

6. A separation analysis of anion a forth in claim 1, in which the Component A is a hydroxytricarboxylic acid.

7. A separation analysis of anions as set forth in claim 1, in which the Component A is a mono-saccharide.

8. A separation analysis of anions as set forth in claim 1, in which a solution prepared from a sulphonate (component A) and an aliphatic monocarboxylic acid (component B) is used as an eluent.

9. A separation analysis of anions as set forth in claim 1, in which a solution prepared from a sulphonate (component A) and boric acid (component B) is used as an eluent.

10. A separation analysis of anions as set forth in claim 1 wherein component B is borax.

11. A separation analysis of anions as set forth in claim 1 in which the component B is boric acid.

12. A separation analysis of anions as st forth in claim 1 in which the component B is an aliphatic monocarboxylic acid selected from the group consisting of forming acid, cetic acid and propionic acid.

13. A separation analysis of anions as set forth in claim 1 for the quantitative analysis of chloride ion, nitrite ion, bromide ion, nitrate ion, sulfate ion, and phosphate ion, in which the eluent comprises as a component A at least one of said aliphatic polycarboxylic acid, aliphatic hydroxcarboxylic acid, aromatic organic acid, saccharide acid and sugar, and the component B comprises at least borax, wherein the concentration of component A and component B is in the range of $1 \times 10^{-4}$ to $5 \times 10^{-3}$ mol, and wherein the eluent has a pH in the range of 7.5–11.0.

14. A separation analysis as set forth in claim 13 wherein the eluent has a pH in the range of 8.5 to 9.5.

15. A separation analysis of anions as set forth in claim 1 wherein the eluent is composed of the sulfonate as component A and component B comprises boric acid or the aliphatic monocarboxylic acid, and wherein the concentration of component A is in the range of $1 \times 10^{-4}$ to $5 \times 10^{-3}$ mol, and the concentration of component B is in the range of $1 \times 10^{-2}$ to $1 \times 10^{-1}$ mol, and wherein the eluent has a pH in the range of 3.0–6.0.

16. A separation analusis of anions as set set forth in claim 15 wherein the pH of the eluent is in the rane of from 4.5 to 5.5.

* * * * *

UNITED STATES PATENT AND TRADEMARK OFFICE
CERTIFICATE OF CORRECTION

PATENT NO.   : 4,500,431
DATED        : February 19, 1985
INVENTOR(S)  : Akiyoshi Miyanaga and Yukitada Kurihara It is certified that error appears in the above-identified patent and that said Letters Patent is hereby corrected as shown below:

Claim 2, line 1, after "separation", delete "a", insert --analysis--.

Claim 4, line 1, delete "anion", insert --anions--.

Claim 5, line 2, delete "dihydroxydioarboxylic", insert --dihydroxydicarboxylic--.

Claim 6, line 1, delete "anion a", insert --anions as set--.

Claim 12, line 3, delete "forming", insert --formic--;
         line 4, delete "cetic", insert --acetic--.

Claim 13, line 4, after "comprises as", delete "a".

Claim 16, line 1, delete "analusis", insert --analysis--;
         line 2, delete "rane", insert --range--.

Signed and Sealed this

Eighteenth Day of June 1985

[SEAL]

Attest:

DONALD J. QUIGG

Attesting Officer    Acting Commissioner of Patents and Trademarks